United States Patent
Hagg et al.

(10) Patent No.: US 7,311,707 B2
(45) Date of Patent: Dec. 25, 2007

(54) CONNECTING DEVICE FOR AN ELECTROSURGICAL INSTRUMENT

(75) Inventors: Martin Hagg, Wannweil (DE); Ralf Kühner, Stuttgart (DE); Uwe Schnitzler, Tübingen (DE)

(73) Assignee: Erbe Elektromedizin GmbH, Tubingen (DE)

( * ) Notice: Subject to any disclaimer, the term of this patent is extended or adjusted under 35 U.S.C. 154(b) by 108 days.

(21) Appl. No.: 10/519,276

(22) PCT Filed: Jun. 26, 2003

(86) PCT No.: PCT/EP03/06795

§ 371 (c)(1),
(2), (4) Date: Dec. 27, 2004

(87) PCT Pub. No.: WO2004/002345

PCT Pub. Date: Jan. 8, 2004

(65) Prior Publication Data
US 2005/0240172 A1    Oct. 27, 2005

(30) Foreign Application Priority Data
Jun. 27, 2002   (DE) .............................. 102 28 791

(51) Int. Cl.
*A61B 18/18* (2006.01)
(52) U.S. Cl. .............................. 606/49; 606/40; 606/46
(58) Field of Classification Search ............ 606/32–38, 606/40, 41; 607/96–100, 101
See application file for complete search history.

(56) References Cited

U.S. PATENT DOCUMENTS

| 4,781,175 A | | 11/1988 | McGreevy et al. |
| 5,061,268 A | * | 10/1991 | Fleenor .................... 606/45 |
| 6,149,648 A | * | 11/2000 | Cosmescu ................. 606/42 |

FOREIGN PATENT DOCUMENTS

| DE | 11 59 574 | 12/1963 |
| DE | 40 38 633 | 11/1992 |

OTHER PUBLICATIONS van Vliet, et al., "The Effect of Argon Gas Flow During Electrosurgery", Proceedings of the 18th Annual International Conference of the IEEE, Engineering in Medicine and biology Society, 1996, Bridging Disciplines for Biomedicine, Oct. 3-Nov. 3, 1996, vol. 1, S. 216-217.

* cited by examiner

Primary Examiner—Michael Peffley
(74) Attorney, Agent, or Firm—Dickstein Shapiro LLP

(57) ABSTRACT

The invention relates to a connecting device for an electrosurgical instrument, which comprises at least one gas supply line and one power supply line. Said connecting device comprises a housing into which passes the gas supply line including the power supply line disposed therein. The connecting device is also provided with a branching device that is located in the housing, and by way of which the power supply line is diverted out of the gas supply line in order to form a gas-connection end piece and a power-connection end piece, and with a plug fixed to the housing in order to make connection to a socket in an appliance or to connecting leads running to the appliance. The gas-connection end piece and the power-connection end piece are coupled to the plug and a filter is disposed within the housing in the gas-connection end piece.

8 Claims, 3 Drawing Sheets

CONNECTING DEVICE FOR AN ELECTROSURGICAL INSTRUMENT

RELATED U.S. APPLICATIONS

Not applicable.

STATEMENT REGARDING FEDERALLY SPONSORED RESEARCH OR DEVELOPMENT

Not applicable.

REFERENCE TO MICROFICHE APPENDIX

Not applicable.

FIELD OF THE INVENTION

The invention relates to a connecting device for an electrosurgical instrument that comprises at least one gas supply line and one power supply line as well as to an APC instrument in combination with such a connecting device.

BACKGROUND OF THE INVENTION

Electrosurgical instruments such as, for example, the APC probes used in endoscopy, frequently comprise a gas conduit through which gas is supplied, and a power supply line that conducts HF electrical current. As a rule, the probes are connected to an electrical appliance that controls the supplies of gas and current, by means of connecting leads.

The patent EP 0447121 A2 discloses a probe connected to such an appliance by connecting devices such that the gas and HF current conducted to the probe in separate connecting devices are not brought together until they are in the vicinity of the front tip of the probe. Therefore, especially when the probe is used in gastroenterology, secretions and fluids from human or animal bodies can enter the gas and power supply lines during treatment and contaminate them. This contamination occurs not only in the parts of the lines that are inside the probe but also in those parts connected to the probe. As a consequence, after such contamination has occurred, both the probe and also the connecting lines must be replaced.

Although the connecting devices disclosed in EP 0447121 A2 for connecting the probe to the leads that come from the appliance incorporate a filter, which is intended to provide protection against such contamination, this filter is positioned in such a way that only the appliance is protected.

Accordingly, it is the object of the present invention to provide a connecting device for an electrosurgical instruments that makes it possible efficaciously to protect the connecting leads associated with the instrument, or integrated therein, against contamination by secretions and fluids from human or animal bodies.

BRIEF SUMMARY OF THE INVENTION

According to the present invention there is provided a connecting device for an electrosurgical instrument that comprises at least one gas supply line and one power supply line, comprising a housing out of which passes a gas supply line with a power supply line disposed within the gas supply line; a branching device located in the housing by way of which the power supply line is diverted out of the gas supply line in order to form respectively a gas-connection end piece and a power-connection end piece; a plug to which the gas-connection end piece and the power-connection end piece are coupled, and which is fastened to the housing in order to make connection with a socket in an appliance or with connecting leads; and a filter disposed within the housing in the gas-connection end piece.

The object of the invention is achieved by disposition of the filter within the housing in the gas-connection end piece. The placement of the filter immediately behind the surgical instrument, which for example can be constructed as a probe or pencil, prevents secretions and fluids from penetrating into the connecting lines and/or the appliance, so that it is unnecessary to exchange the connecting leads after the operation has been completed.

It is advantageous for the branching device to comprise a first aperture into which the gas supply line, together with the power supply line disposed therein, can be inserted like a plug, as well as a second aperture into which the filter can be similarly inserted. This enables a simple and rapid exchange, after a preferably predetermined period of use, of either the branching device including the filter or the filter by itself. For this exchanging procedure the housing must be opened, the relevant elements removed and their replacements inserted, and the housing closed gain. Thus the filter can be readily replaced before a filter element contained therein becomes oversaturated.

According to a preferred embodiment the branching device comprises an integrated cable channel to accommodate the diverted power supply line. The cable channel assists stable positioning of the power supply line within the branching device and hence contributes to forming a transition region, i.e. the region in which the power supply line branches off, that is not vulnerable to damage.

The electrosurgical instrument can be designed for single use, as it can be rapidly and simply uncoupled from the connecting device, by way of a plug-and-socket arrangement, and a new instrument connected to the device.

Preferably the connecting device is used for an APC instrument, which can be an APC probe.

The present invention will now be described by way of example with reference to the accompanying drawings.

DETAILED DESCRIPTION OF THE INVENTION

Figure 1:
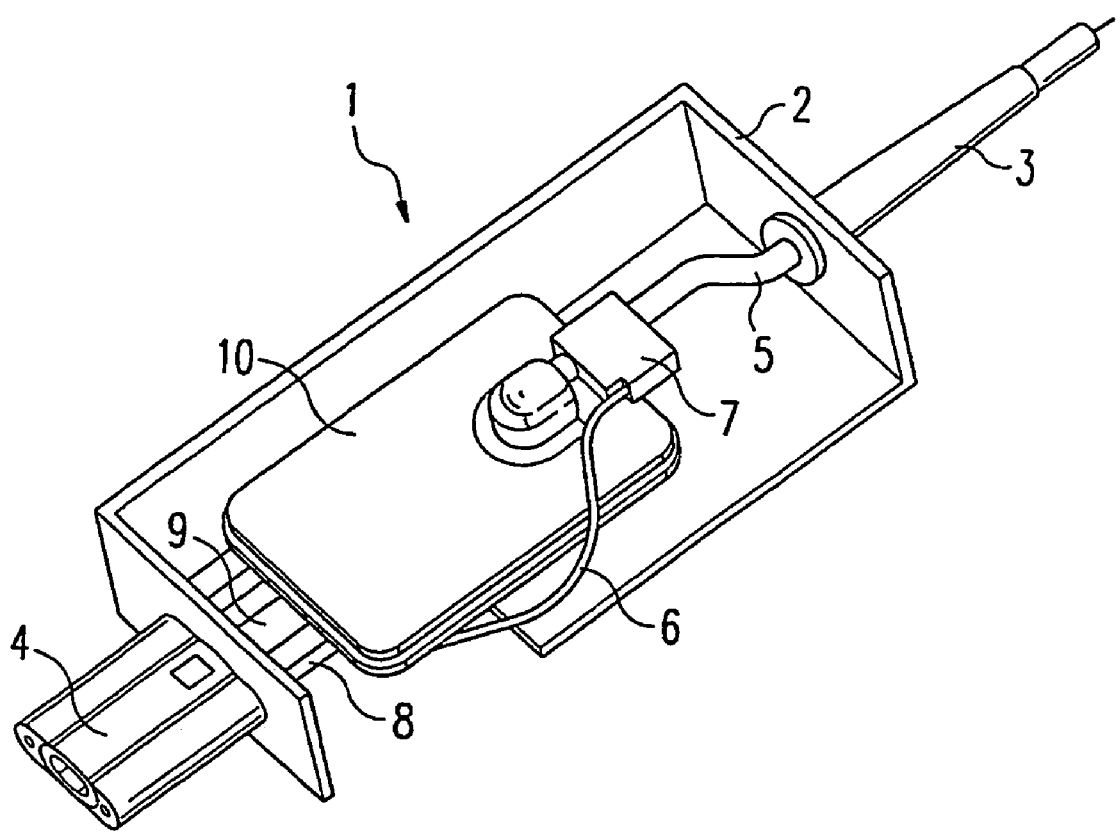
FIG. 1 shows an embodiment of the connecting device in accordance with the invention, partially opened, in perspective plan view.

In FIG. 1, an embodiment of the connecting device in accordance with the invention is shown in perspective. The connecting device 1 comprises a housing, only part of which is shown here; normally the housing completely encloses its contents. The housing 2 can be opened and closed again by means of a sliding mechanism or flap, in order to provide access to the elements contained in the housing 2, in particular a filter.

A probe 3 is attached, preferably releasably, to the housing at one of its ends. At another end of the housing is disposed a plug arrangement 4 designed to be inserted into a socket in an appliance or attached to connecting leads that run to that appliance.

A gas supply line 5 connected to the probe 3 encloses a power supply line 6. Both supply lines are connected to a branching device 7 by means of which the power supply line 6 is guided out of the gas supply line 5 to form a power-connection end piece 8 and a gas-connection end piece 9.

Between the gas-connection end piece 9 and the branching device 7 a filter 10 is disposed in such a way that it can be exchanged.

Figure 2:
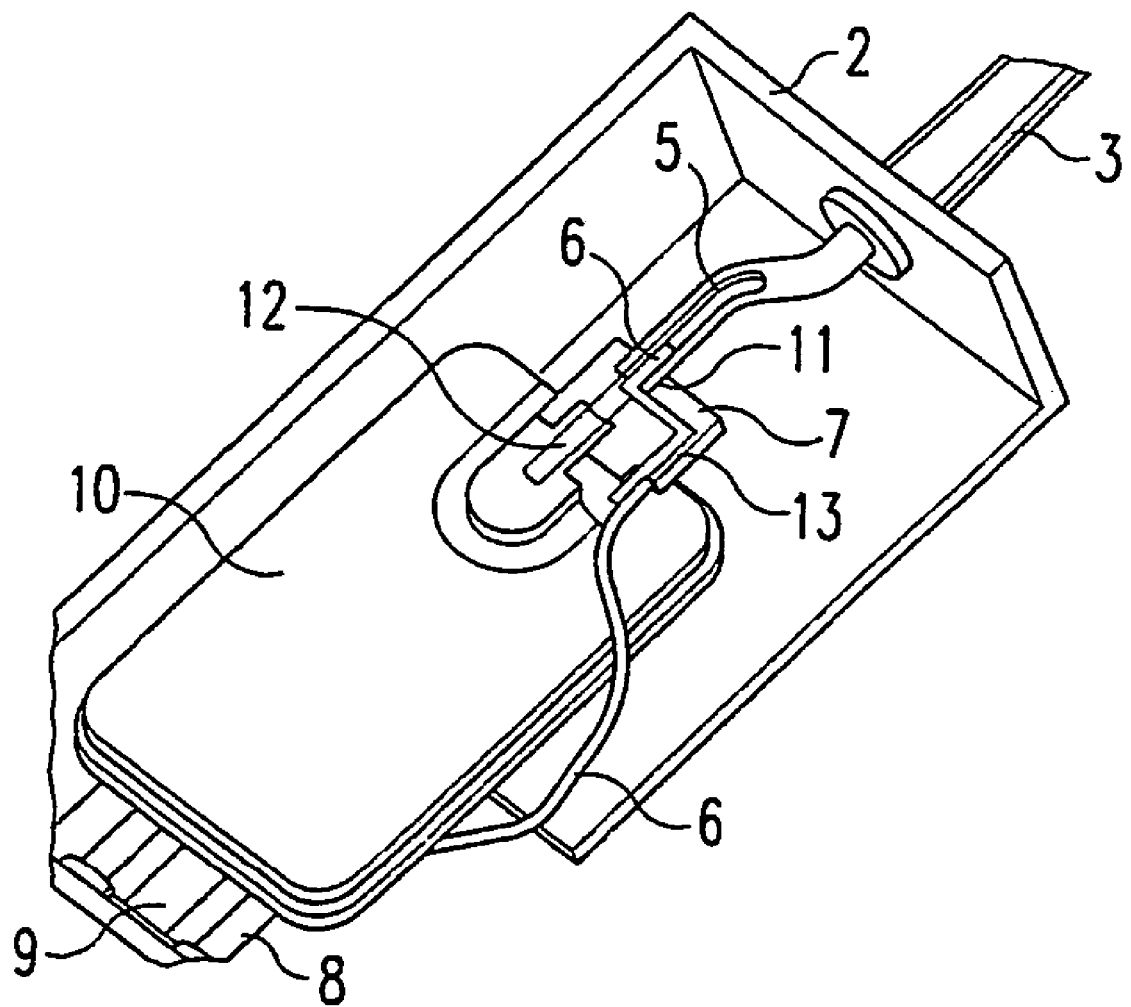
FIG. 2 is an enlarged drawing of part of the embodiment of the connecting device in accordance with the invention shown in FIG. 1.

FIG. 2 is an enlarged perspective plan view of part of the connecting device shown in FIG. 1. It can be seen in FIG. 2 that the gas supply line 5 with the power supply line 6 disposed therein is connected to the branching device 7 by way of an aperture 11 in the branching device, like a plug in a socket. Into a second aperture 12 of the branching device 7 the filter 10 has been inserted.

Having branched away from the gas supply line 5, the power supply line 6 is guided within a cable channel 13 disposed in the branching device 7 in such a way that it pass around the filter 10 with no further guidance, until it reaches the power-connection end piece 8. This makes it possible to exchange the filter 10 situated between the branching device 7 and part of the gas-connection end piece 9, with no need to interrupt the power supply line 6.

Figure 3:
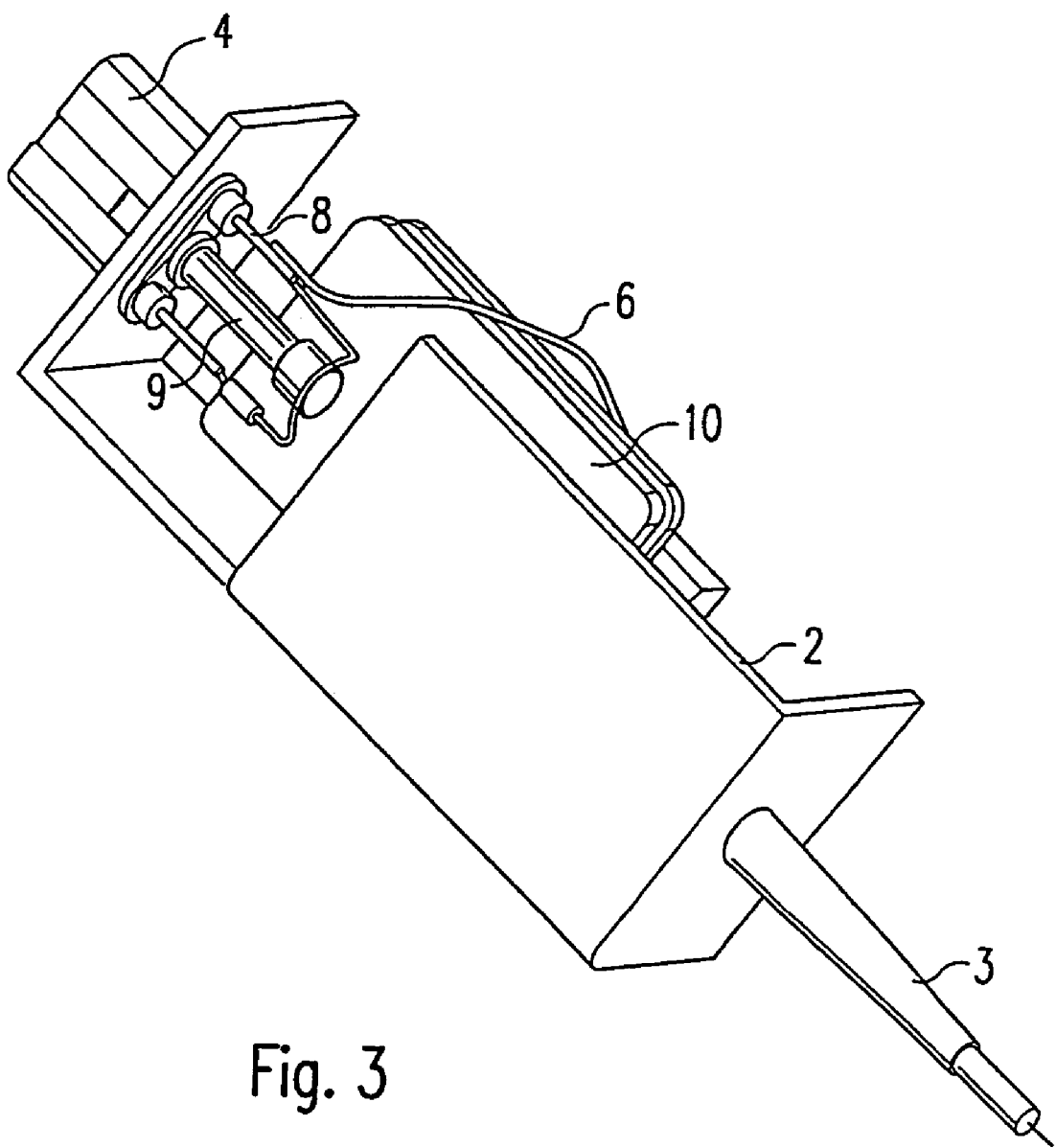
FIG. 3 shows a perspective view of the underside of the embodiment of the connecting device in accordance with the invention shown in FIGS. 1 and 2.

In FIG. 3 the underside of the embodiment of the connecting device according to FIGS. 1 and 2 is shown in perspective. This drawing makes clearer that the filter 10 opens into part of the gas connection end piece 9, while the power supply line 6 opens into power-connection end piece 8 on the underside of the housing. Hence the connection end pieces 8 and 9 do not impede the process of exchanging the filter 10, inasmuch as the filter 10 is removed and re-inserted from above the housing.

The gas-connection end piece 9 and the power-connection end piece 8 are attached to the plug 4 so that they can be connected to connecting leads.

LIST OF REFERENCE NUMERALS

1 Connecting device
2 Housing
3 Probe
4 Plug
5 Gas supply line
6 Power supply line
7 Branching device
8 Power-connection end piece
9 Gas-connection end piece
10 Filter
11 First aperture
12 Second aperture
13 Cable channel

The invention claimed is:

1. Connecting device for an electrosurgical instrument that comprises at least one gas supply line and one power supply line, comprising:
   a housing out of which passes a gas supply line with a power supply line disposed within the gas supply line;
   a branching device located in the housing by way of which the power supply line is diverted out of the gas supply line in order to form respectively a gas-connection end piece and a power-connection end piece;
   a plug to which the gas-connection end piece and the power-connection end piece are coupled, an which is fastened to the housing in order to make connection with a socket in an appliance or with connecting leads; and
   a filter disposed within the housing in the gas-connection end piece.

2. Connecting device according to claim 1, wherein the filter is exchangeable.

3. Connecting device according to claim 1, wherein the branching device defines a first aperture into which the gas supply line with the power supply line disposed therein is inserted in the manner of a plug into a socket.

4. Connecting device according to claim 1, wherein the branching device defines a second aperture into which the filter is inserted in the manner of a plug into a socket.

5. Connecting device according to claim 1, wherein the branching device defines an integrated cable channel to accommodate the power supply line.

6. Connecting device according to claim 1, adapted for connection to a single use electrosurgical instrument.

7. An APC instrument comprising:
   at least one gas supply line and one power supply line in combination with a connecting device comprising a housing out of which passes the gas supply line with the power supply line disposed within the gas supply line;
   a branching device located in the housing by way of which the power supply line is diverted out of the gas supply line in order to form respectively a gas-connection end piece and power-connection end piece;
   a plug to which the gas-connection end piece and the power-connection end piece are coupled, and which is fastened to the housing in order to make connection with connecting leads; and
   a filter disposed within the housing in the gas-connection end piece.

8. An APC instrument according to claim 7, in the form of an APC probe.

* * * * *